United States Patent
Tan (10) Patent No.: US 11,826,277 B2
(45) Date of Patent: *Nov. 28, 2023

(54) CUSTOMIZABLE STOMA INSERT

(71) Applicant: Jason Jit-Sun Tan, West Leederville (AU)

(72) Inventor: Jason Jit-Sun Tan, West Leederville (AU)

(*) Notice: Subject to any disclaimer, the term of this patent is extended or adjusted under 35 U.S.C. 154(b) by 25 days.

This patent is subject to a terminal disclaimer.

(21) Appl. No.: 17/530,234

(22) Filed: Nov. 18, 2021

(65) Prior Publication Data

US 2022/0117772 A1 Apr. 21, 2022

Related U.S. Application Data

(63) Continuation of application No. 16/063,826, filed as application No. PCT/AU2016/061262 on Dec. 21, 2016, now Pat. No. 11,207,205.

(30) Foreign Application Priority Data

Dec. 24, 2015 (AU) .............................. 2015905416

(51) Int. Cl.
*A61F 5/445* (2006.01)
*A61F 5/443* (2006.01)
(Continued)

(52) U.S. Cl.
CPC .............. *A61F 5/445* (2013.01); *A61F 5/441* (2013.01); *A61F 5/443* (2013.01); *B33Y 50/00* (2014.12);
(Continued)

(58) Field of Classification Search
CPC .......... A61F 5/445; A61F 5/441; A61F 5/443; B33Y 50/00; B33Y 80/00
See application file for complete search history.

(56) References Cited

U.S. PATENT DOCUMENTS 4,708,966 A 11/1987 Oomans et al.
4,985,459 A 1/1991 Sunshine et al.
(Continued)

FOREIGN PATENT DOCUMENTS

WO 2006/032904 A2 3/2006
WO WO-2006032904 A2 * 3/2006 ............. A61B 17/60

OTHER PUBLICATIONS

European Communication pursuant to Article 94(3) EPC for European Application No. 16877000, dated Jan. 13, 2021, 4 pages,.
(Continued)

*Primary Examiner* — Guy K Townsend
(74) *Attorney, Agent, or Firm* — TraskBritt (57) ABSTRACT

The disclosure relates to a method of manufacturing a custom stoma insert for a patient having a stoma, as well as to a stoma made using the method of the disclosure. The method comprises the steps of scanning the stoma and surrounding skin area to generate a three-dimensional scan of the area for which the stoma insert is to be manufactured; manipulating scan data obtained from the three-dimensional scan to render a three-dimensional model of the stoma and surrounding skin contours, such that the scan data is suitable for use in an additive manufacturing environment; creating a custom mold for the stoma insert using additive manufacturing such that the mold provides a complementary surface closely mirroring the contours of the stoma and surrounding skin area; and producing the stoma insert by casting a physiologically acceptable moldable material into the custom mold.

20 Claims, 3 Drawing Sheets

(51) Int. Cl.
*A61F 5/441* (2006.01)
*B33Y 50/00* (2015.01)
*B33Y 80/00* (2015.01)
*B33Y 10/00* (2015.01)
*B29C 33/38* (2006.01)

(52) U.S. Cl.
CPC ....... *B33Y 80/00* (2014.12); *A61F 2005/4455* (2013.01); *B29C 33/3842* (2013.01); *B33Y 10/00* (2014.12)

(56) References Cited

U.S. PATENT DOCUMENTS

| | | | | |
|---|---|---|---|---|
| 10,070,987 | B2* | 9/2018 | Scott | A61F 5/449 |
| 10,722,562 | B2* | 7/2020 | Pedersen | A61P 31/04 |
| 10,918,847 | B2* | 2/2021 | Stynes | A61F 2/78 |
| 11,207,205 | B2* | 12/2021 | Tan | A61F 5/445 |
| 11,337,858 | B2* | 5/2022 | Schwartz | A61F 9/02 |
| 2005/0154361 | A1* | 7/2005 | Sabesan | A01N 43/16 |
| | | | | 424/618 |
| 2005/0175665 | A1* | 8/2005 | Hunter | A61L 31/16 |
| | | | | 514/49 |
| 2005/0175703 | A1* | 8/2005 | Hunter | A61L 31/16 |
| | | | | 514/453 |
| 2005/0178395 | A1* | 8/2005 | Hunter | A61L 31/16 |
| | | | | 128/898 |
| 2005/0178396 | A1* | 8/2005 | Hunter | A61L 27/54 |
| | | | | 128/898 |
| 2005/0182463 | A1* | 8/2005 | Hunter | A61K 45/06 |
| | | | | 604/8 |
| 2005/0183731 | A1* | 8/2005 | Hunter | A61L 31/16 |
| | | | | 623/13.11 |
| 2005/0186244 | A1* | 8/2005 | Hunter | A61K 45/06 |
| | | | | 514/17.1 |
| 2005/0187140 | A1* | 8/2005 | Hunter | A61L 27/54 |
| | | | | 606/76 |
| 2005/0196421 | A1* | 9/2005 | Hunter | A61L 27/54 |
| | | | | 604/500 |
| 2005/0208095 | A1* | 9/2005 | Hunter | A61P 31/00 |
| | | | | 424/423 |
| 2006/0177489 | A1* | 8/2006 | Massouda | C08J 7/0427 |
| | | | | 424/443 |
| 2008/0275327 | A1* | 11/2008 | Faarbaek | A61B 5/6833 |
| | | | | 600/382 |
| 2010/0030167 | A1* | 2/2010 | Thirstrup | A61F 5/4404 |
| | | | | 340/657 |
| 2011/0212090 | A1 | 9/2011 | Pedersen et al. | |
| 2012/0052040 | A1* | 3/2012 | Hunter | A61L 31/16 |
| | | | | 514/274 |
| 2014/0236335 | A1* | 8/2014 | Lewis | A61F 5/445 |
| | | | | 700/98 |
| 2014/0276500 | A1* | 9/2014 | Scott | A61F 5/4404 |
| | | | | 604/338 |
| 2014/0288381 | A1* | 9/2014 | Faarbaek | A61B 5/0002 |
| | | | | 600/300 |
| 2016/0263366 | A1* | 9/2016 | Stynes | A61M 39/0247 |
| 2018/0200113 | A1* | 7/2018 | Schwartz | A61F 9/026 |
| 2019/0015243 | A1* | 1/2019 | Scott | A61F 5/449 |
| 2019/0175386 | A1* | 6/2019 | Monty | A61F 5/445 |
| 2019/0374163 | A1* | 12/2019 | Faarbaek | A61B 5/0002 |
| 2020/0281758 | A1* | 9/2020 | Tan | B33Y 80/00 |
| 2021/0022683 | A1* | 1/2021 | Faarbaek | A61B 5/411 |
| 2022/0117772 | A1* | 4/2022 | Tan | A61F 5/441 |

OTHER PUBLICATIONS

International Search Report for International Application No. PCT/AU2016/051262, dated Feb. 27, 2017, 4 pages.
International Written Opinion for International Application No. PCT/AU2016/051262, dated Feb. 27, 2017, 6 pages.
Rainsford "Anti-Inflammatory and Anti-Rheumatic Drugs," vol. I-III, CRC Press, Boca Raton (1985) text book—Cover only.
Remington's Pharmaceutical Sciences, 18th Edition, pp. 1173-1232 (1990), text book, Cover page only.
Scherrer et al. "Anti-Inflammatory Agents, Chemistry and Pharmacology" Academic Press, New York (1974), text book, cover only.
Supplementary European Extended Search Report and Opinion for European Application No. 16877000, dated Nov. 5, 2019, 5 pages.

* cited by examiner

CUSTOMIZABLE STOMA INSERT

CROSS-REFERENCE TO RELATED APPLICATIONS

This application is continuation of U.S. patent application Ser. No. 16/063,826, filed Jun. 19, 2018, now U.S. Pat. No. 11,207,205, issued Dec. 28, 2021, which is a national phase entry of International Patent Application PCT/AU2016/051262, filed Dec. 21, 2016, designating the United States of America and published as International Patent Publication WO 2017/106911 A1 on Jun. 29, 2017, which claims the benefit under Article 8 of the Patent Cooperation Treaty to Australian Patent Application Serial No. 2015905416, filed Dec. 24, 2015, the disclosure of each of which is hereby incorporated herein in its entirety by this reference.

TECHNICAL FIELD

This disclosure relates to a customizable stoma insert and to a method of manufacturing a stoma insert.

BACKGROUND

The following discussion of the background art is intended to facilitate an understanding of the present disclosure only. No acknowledgement or admission that any of the material referred to is or was part of the common general knowledge as at the priority date of the application is intended.

A stoma is an artificial opening made into a hollow organ, especially one on the surface of the body leading to the gut or trachea. This is usually done to create a passage or aperture for drainage or other purposes. As such, a well-known form of an artificial stoma is a colostomy, which is a surgically created opening in the large intestine that allows the removal of feces or other excreta out of the body, bypassing the rectum, to drain into an ostomy pouch or other collection device. This is done as a surgical procedure in which a stoma is formed by drawing the healthy end of the large intestine or colon through an incision in the anterior abdominal wall and suturing it into place. This opening, in conjunction with an attached stoma appliance, provides an alternative channel for feces or other excreta to leave the body but conventional systems of which the applicant is aware frequently lead to spillage, odor escape, and excessive inflammation between the stoma and the ostomy pouch.

It is an objective of the disclosure described herein to address aspects of this problem.

BRIEF SUMMARY

According to one aspect of the disclosure there is provided a method of manufacturing a custom stoma insert for a patient having a stoma, the method comprising the steps of:
scanning the stoma and surrounding skin area to generate a three-dimensional scan of the area for which the stoma insert is to be manufactured;
manipulating scan data obtained from the three-dimensional scan to render a three-dimensional model of the stoma and surrounding skin contours, such that the scan data is suitable for use in an additive manufacturing environment;
creating a custom mold for the stoma insert using additive manufacturing such that the mold provides a complementary surface closely mirroring the contours of the stoma and surrounding skin area; and
producing the stoma insert by casting a physiologically acceptable moldable material into the custom mold, allowing the moldable material to solidify to a desired solidity, and removing the custom stoma insert from the mold, the resultant custom stoma insert being shaped and dimensioned to ensure a snug fit within the stoma and over the skin surrounding the stoma.

The step of creating the custom mold may be accomplished using 3D-printing as a form of additive manufacturing.

Advantageously, the mold may be manufactured from conventional commercially available 3D-printing polymers or compounds, thereby eliminating added expenses and complexity during the manufacturing of the stoma insert.

The mold may include a central pillar that corresponds generally to the size of the stoma. The central pillar may, in one embodiment of the disclosure, be slightly larger than the stoma to which the stoma insert is to be fitted, such that, when the stoma insert is removed from the mold it defines a central aperture having a cross-sectional diameter similar to, or slightly larger than, the cross-sectional diameter of the stoma, thereby to ensure a slight friction fit or slight interference fit between the stoma insert and the stoma.

In certain embodiments the mold does not include a central pillar, with the resultant custom insert then being in the form of a blind plug that can be used to reduce herniation from the stoma.

The mold may have a cross-sectional diameter similar to, or slightly larger than, the opening of an ostomy bag or pouch that is to be fitted to the ostomy insert. In this way, the ostomy pouch or bag is retained proximal the stoma, with minimal discomfort to the patient.

Advantageously, the mold may have included therein raised or striated areas that, when the stoma insert has been molded, produces a complementary hatched, scored, or striated surface on a skin-contacting face of the stoma insert. The hatched, scored, or striated surface assists with channeling sweat, sebum, and other bodily fluids away from the stoma and assists in keeping the area dry while retaining sufficient purchase when located on the skin of the patient.

The surface finish of the mold can be smoothed, roughed, or improved as required using chemical vapor processes, or may be coated with a non-stick or low-stick compound such as polytetrafluoroethylene, if desired.

The mold may generally be shaped and dimensioned to further allow for the inclusion of a circumferentially-extending collar surrounding a core of the stoma insert during the molding process, the collar area of the molded stoma insert in turn being shaped and dimensioned to at least partially cover an area surrounding the stoma sufficiently to ensure sufficient purchase of an ostomy bag on the stoma insert.

Similar to the stoma insert core, the circumferentially-extending collar may also be shaped and dimensioned to snugly follow the contours of the area surrounding the stoma in the patient, thereby ensuring a snug or light-pressure suction fit between the stoma insert and the stoma core.

The stoma insert core and collar may be molded in unitary fashion. Alternatively, the stoma insert core and collar may be molded in non-unitary fashion. If molded in non-unitary fashion, the stoma insert and the collar may each be made of moldable materials having differing physico-chemical properties. As such, the stoma insert core may be made of a material that is more pliant and resiliently flexible than the material used for the stoma insert collar.

Scanning the stoma and surrounding skin area may be accomplished using surface scanning technology, particularly 3D-scanning techniques. The 3D-scanning techniques may be selected from optical, X-ray, laser, photoacoustics, blue or white light 3D-scanning, LIDAR, optical coherence tomography, or MRI. In a preferred embodiment, scanning is done using tomography, particularly computerized tomography ("CT"), computerized axial tomography ("CAT") or cone beam computed tomography ("CBCT"). This is typically accomplished in high resolution of scan slices of 2 mm thickness or less. The scanning process is performed to create a point cloud of geometric samples of the stoma and surrounding skin surface of the patient. These points can then be used to extrapolate the shape of the stoma and surrounding skin area, for use in 3D-printing the mold for the stoma insert.

Accordingly, the step of manipulating the data may be accomplished by bringing the scan data into a form suitable for use in 3D-printing, typically using software designed for medical imaging and/or which converts data in DICOM format to a surface render as an STL file.

In one embodiment of the disclosure, the stoma insert may be cast using any one or more of natural rubber, latex, neoprene, polyvinyl chloride, nitrile, synthetic polymer, synthetic resin, synthetic rubber, acrylic-based polymers, or any mixtures thereof. In a preferred embodiment the stoma insert may be cast using silicone rubber.

The stoma insert may be impregnated or coated with an antimicrobial compound. The antimicrobial compound may be selected from any one or more or naturally occurring, elemental, or synthetic antimicrobial compounds such as antibacterial, bacteriostatic, bacteriolytic, antiviral, and/or antifungal compounds, including silver salts or ions.

The antimicrobial agent may be present from about 0.001 wt. % to 5 wt. % of the total weight of the stoma insert. Preferably, the antimicrobial agent is present from about 0.01 wt. % to 1.0 wt. % of the total weight of the insert. More preferably, the antimicrobial agent is present from about 0.02 wt. % to 0.5 wt. % of the total weight of the insert. A stoma insert with an amount of antimicrobial agent up to about 5 wt. % not only has an effective antimicrobial effect on surfaces of the insert, but also has an antimicrobial effect on surfaces contacted by the insert. Therefore, harmful microbial entities are not only prevented from being transferred from the stoma insert to the skin surface or stoma walls contacted, but microbial entities on that surface may also be reduced, kept static, or eliminated following contact.

In one embodiment, the stoma insert is coated over at least a part thereof with antibodies directed against microbes, particularly antibodies that can bind to, and sequester, microbes that are multiply resistant to current antimicrobials.

The stoma insert may be impregnated or coated with an anti-inflammatory, antipyretic, or analgesic compound, such as a non-steroidal anti-inflammatory drug ("NSAID"). The NSAID may be selected from any one or more naturally occurring or synthetic NSAID compounds. Examples of preferred NSAIDs useful in the present disclosure include, but are not limited to: acetylsalicylic acid, ibuprofen, fenbuprofen, fenoprofen, flurbiprofen, indomethacin, ketoprofen, naproxen, their pharmaceutically-acceptable salts, enantiomers thereof, and mixtures thereof. Ibuprofen, indomethacin, acetylsalicylic acid, and naproxen are especially preferred for use in the present disclosure. In certain embodiments, an anti-rash cream or barrier cream, typically including zinc, may be used with, incorporated into, or impregnated into the stoma insert to assist with healing and protection of skin.

The stoma insert may be impregnated or coated with one or more deodorant compounds.

Furthermore, the stoma insert may be coated or impregnated with a low-tack, physiologically acceptable adhesive that may assist in locating the insert to the stoma or surrounding area.

Advantageously, the stoma insert may also be coated or impregnated with an antiperspirant compound to control perspiration underneath the stoma insert and to prevent body odor from perspiration or sebaceous excretions of the skin surrounding the stoma, covered by the stoma insert of the disclosure.

The deodorant, anti-inflammatory, adhesive, antiperspirant, or antimicrobial compounds, as well as the antibodies, may be admixed with the moldable material or may be fused, typically thermally fused, to the custom insert during manufacture. The deodorant, antibodies, anti-inflammatory, and/or antimicrobial compounds may, in another aspect of the disclosure, be coated on to the mold, so that the compounds are transferred to the insert during the molding process.

When adding a pharmaceutical or medical compound, it is advantageous to impregnate or coat the core of the stoma insert which nests inside the stoma (i.e., bowel opening) or proximal thereto, as many pharmaceutical or medical compounds are not absorbed by skin but rather by the mucosa of bowel. In this example, a slow-release formulation, similar to suppository formulations, may be used to extend the release of the compounds from the stoma insert. Furthermore, compounds that protect the skin may be used, applied to, or impregnated into the stoma insert collar, in other words, the disclosure extends to differential impregnation or coating of the stoma insert in different parts thereof.

The stoma insert may be made from opaque materials but may, in accordance with another aspect of the disclosure, be made from transparent materials such that the skin surrounding the stoma may be visible through the insert to allow a care-giver to readily determine whether the skin is inflamed or otherwise subject to an insult or pathological condition which would not readily be discerned without otherwise first having to remove the stoma insert of the disclosure from the stoma.

According to another aspect of the disclosure, there is provided a method of fitting an ostomy bag to a patient, the method including the steps of manufacturing a stoma insert in accordance with the disclosure as described herein, fitting the stoma insert to a patient, and attaching an ostomy bag to the stoma insert once it has been fitted to the patient.

The method of fitting the ostomy bag to the patient may include the step of first providing a bedding material, such as a putty or silicone paste, surrounding the stoma insert, prior to fitment of the ostomy bag.

BRIEF DESCRIPTION OF THE DRAWINGS

Further features of the present disclosure are more fully described in the following description of several non-limiting embodiments included solely for the purposes of exemplifying the present disclosure. The following description is not a restriction on the broad summary, disclosure or description of the disclosure as set out above and is made with reference to the accompanying drawings in which.

In the figures, incorporated to illustrate features of an example embodiment, like reference numerals are used to identify like parts throughout.

DETAILED DESCRIPTION

Throughout this specification, unless the context requires otherwise, the word "comprise" or variations such as "comprises" or "comprising," or "include" or variations such as "includes" or "including" will be understood to imply the inclusion of a stated integer or group of integers but not the exclusion of any other integer or group of integers.

The following modes, given by way of example only, are described in order to provide a more precise understanding of the subject matter of a preferred embodiment or embodiments. The term "3D-printing" as used herein refers to the process of adding successive layers of a material under computer control to create an object. Therefore, 3D-printing may encompass any of the following types, technologies, and materials, shown in Table 1 below.

TABLE 1

| Type | Technologies | Materials |
|---|---|---|
| Extrusion | Fused deposition modeling (FDM) or Fused Filament Fabrication (FFF) | Thermoplastics, eutectic metals, edible materials, Rubbers, Modeling clay, Plasticine, Metal clay (including Precious Metal Clay) |
| | Robocasting or Direct Ink Writing (DIW) | Ceramic materials, Metal alloy, cermet, metal matrix composite, ceramic matrix composite |
| Light polymerized | Stereolithography (SLA) | Photopolymer |
| | Digital Light Processing (DLP) | Photopolymer |
| Powder Bed | Powder bed and inkjet head 3D printing (3DP) | Almost any metal alloy, powdered polymers, Plaster |
| | Electron-beam melting (EBM) | Almost any metal alloy including Titanium alloys |
| | Selective laser melting (SLM) | Titanium alloys, Cobalt Chrome alloys, Stainless Steel, Aluminum |
| | Selective heat sintering (SHS) | Thermoplastic powder |
| | Selective laser sintering (SLS) | Thermoplastics, metal powders, ceramic powders |
| | Direct metal laser sintering (DMLS) | Almost any metal alloy |

TABLE 1-continued

| Type | Technologies | Materials |
|---|---|---|
| Laminated | Laminated object manufacturing (LOM) | Paper, metal foil, plastic film |
| Wire | Electron beam freeform fabrication (EBF$^3$) | Almost any metal alloy |

Figure 1A:
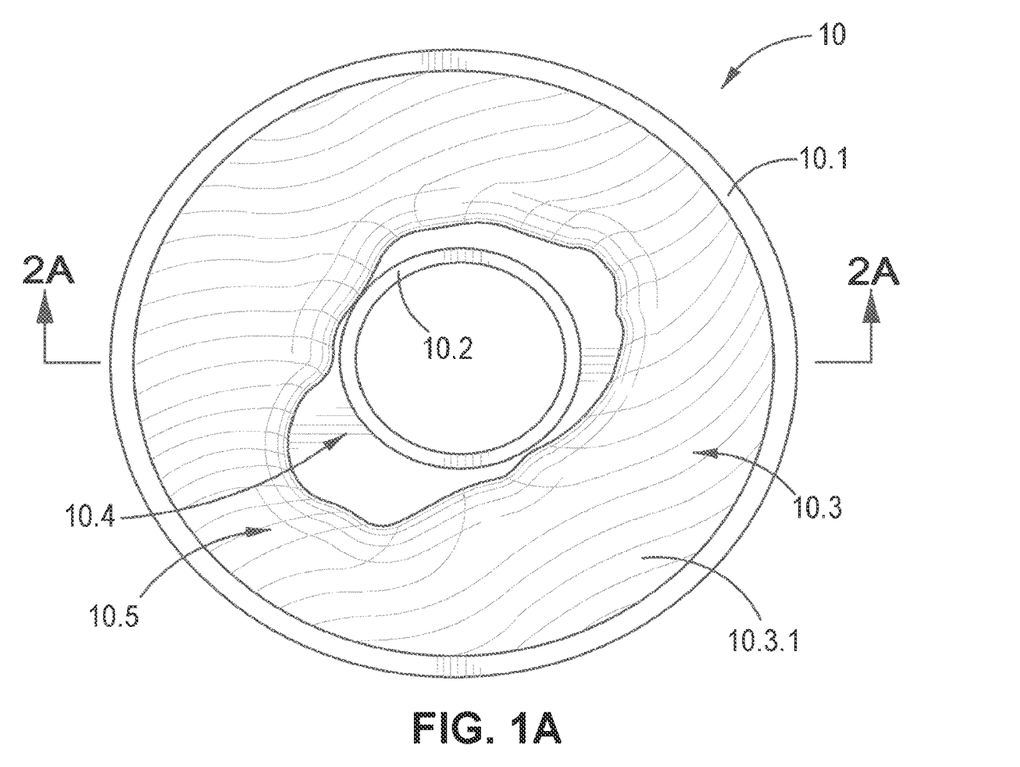
FIG. 1A is a top plan view of a custom ostomy insert mold, made in accordance with an aspect of the disclosure.
Figure 1B:
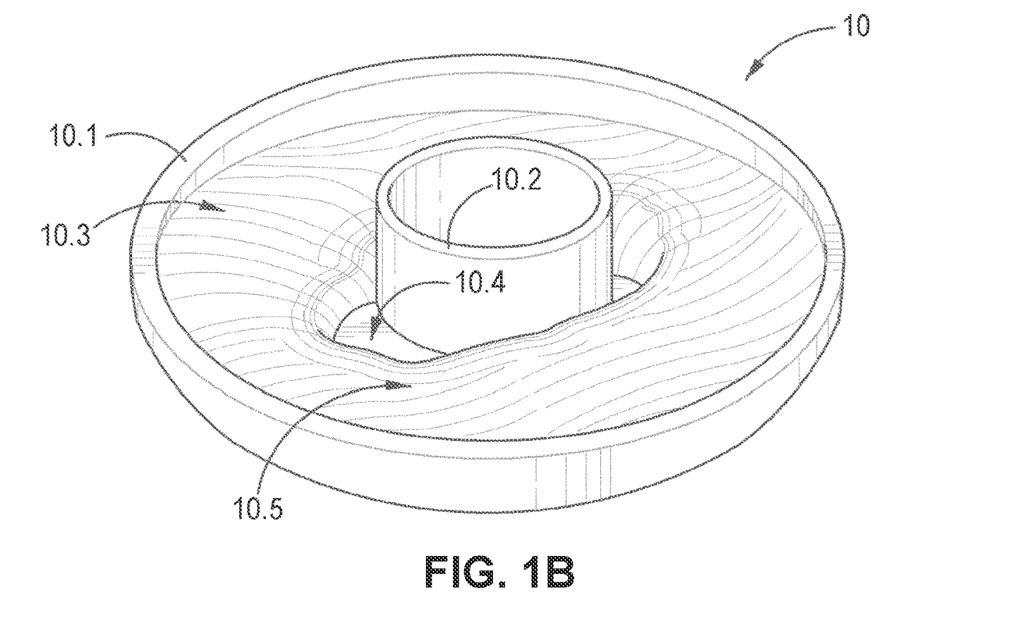
FIG. 1B is a three-dimensional view of a custom ostomy insert mold, made in accordance with an aspect of the disclosure.

Referring now to FIGS. 1A and 1B of the drawings, there is shown a customized 3D-printed mold, generally referred to by reference numeral 10, the mold 10 having been created by performing a CT-scan of a stoma 14 and surrounding skin area 14.1 of a patient 16 (best shown in FIGS. 4, 5, and 6), generating a CT scan data file, manipulating the CT scan data contained in the scan data file to render the data suitable for 3D-printing, and then printing the mold 10 for a custom stoma insert (generally indicated by reference numeral 12 in FIGS. 2A, 2B 3, 4, and 5) for fitment to the stoma 14 of the patient 16.

Figure 6:
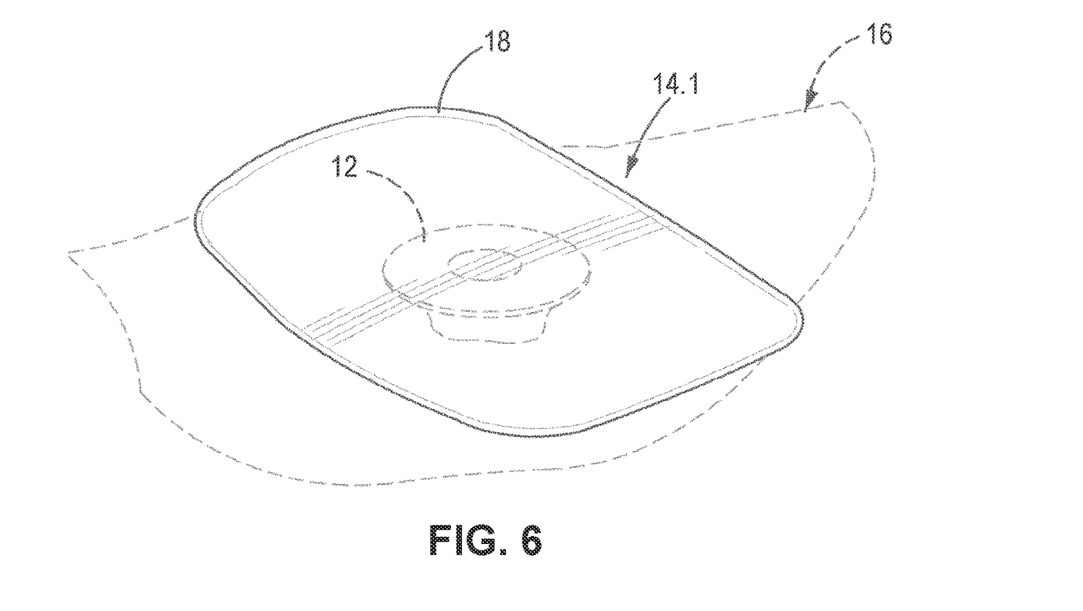
FIG. 6 is a diagrammatic representation of a custom molded stoma insert in accordance with one aspect of the disclosure having an ostomy bag or pouch fitted thereto.

The mold 10 includes a peripheral, raised, circumferentially extending skirt 10.1 that defines an outer boundary for the eventual molded stoma insert 12, and is similar in internal cross-section to an opening of an ostomy pouch or bag (generally indicated by reference numeral 18 in FIG. 6).

Figure 3:
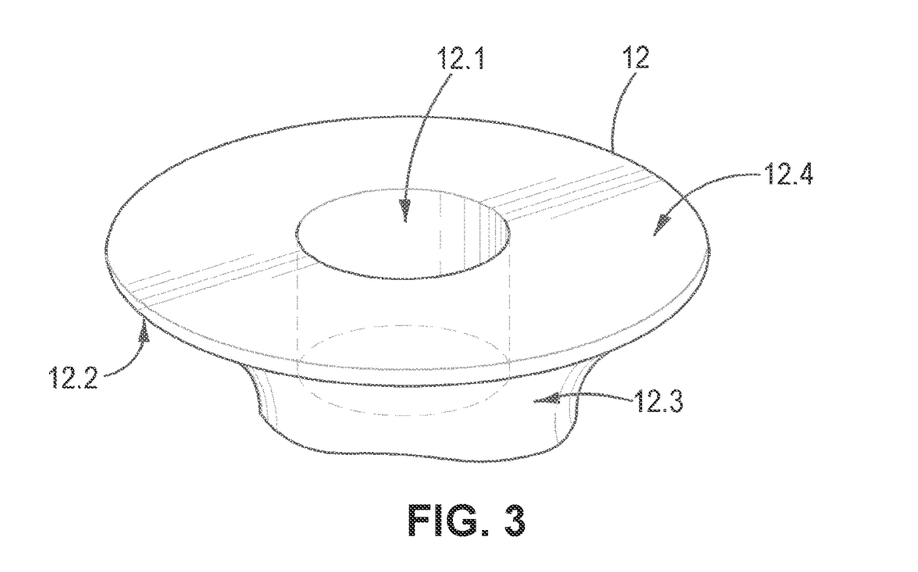
FIG. 3 is a three-dimensional view of a custom molded stoma insert in accordance with one aspect of the disclosure.

The mold 10, further includes a central, generally upright pillar 10.2, which is shaped and dimensioned to be similar, or slightly larger, in cross-sectional diameter than the stoma to which the eventual molded stoma insert 12 is to be fitted. In this way, when the stoma insert 12 is removed from the mold 10, the stoma insert 12 defines a central or offset (as dictated by the mold 10 and stoma 14) aperture 12.1 which provides a fluid flow connection between the interior of the patient 16 and the eventual ostomy pouch 18 fitted to the stoma insert 12.

Figures 4, 5:
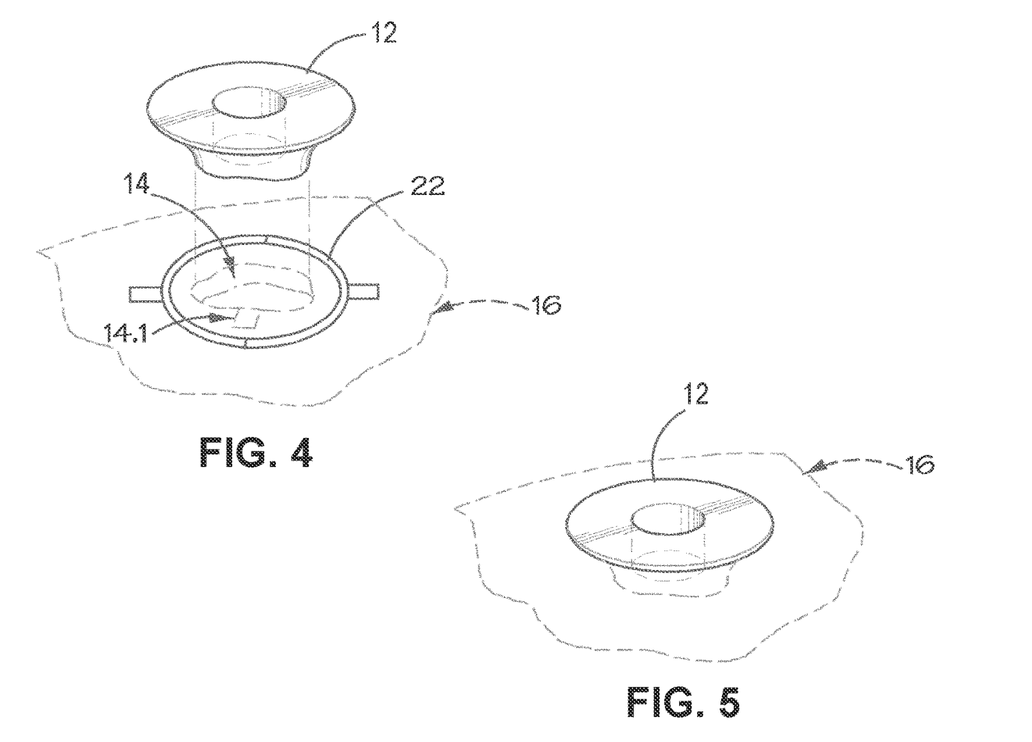
FIG. 4 is a diagrammatic representation of a custom molded stoma insert in accordance with one aspect of the disclosure being fitted to a stoma of a patient.
FIG. 5 is a diagrammatic representation of a custom molded stoma insert in accordance with one aspect of the disclosure when fitted to a stoma of a patient.

An advantage of the disclosure is that the mold 10 is shaped to provide an accurate, though mirrored, representation of the patient's stoma 14 and the surrounding skin area 14.1 surrounding the stoma 14, such that when the stoma insert 12 is fitted to the stoma 14, it provides a snug or light pressure suction fit to the stoma 14 and surrounding skin 14.1 of the patient 16.

By way of overview, the method in accordance with one aspect of the disclosure of making a custom stoma insert 12 for a patient 16 having a stoma 14 thus generally comprises the steps of scanning the stoma 14 and surrounding skin area 14.1 of the patient 16 to generate a three-dimensional scan of the area for which the stoma insert is to be manufactured; manipulating the scan data obtained from the three-dimensional scan to render a three-dimensional model of the stoma 14 and surrounding skin area 14.1 contours, such that the scan data is suitable for use in 3D-printing; creating a custom mold 10 for the stoma insert 12 using 3D-printing such that the mold 10 provides a complementary surface 10.3 closely mirroring the contours of the stoma 14 and surrounding skin area 14.1; and producing the stoma insert 12 by casting a physiologically acceptable moldable material (generally indicated by reference numeral 20 in FIG. 2B), into the custom mold 10, allowing the moldable material 20 to solidify to a desired solidity, and removing the custom stoma insert 12 from the mold 10, the resultant custom stoma insert 12 being shaped and dimensioned to ensure a snug fit within the stoma 14 and over the skin area 14.1 surrounding the stoma 14.

The mold 10 is made using conventional, commercially available polymers used in 3D-printing. This means that a customized ostomy insert 12 can be created within a few hours of receiving CT-scan data of a patient's stoma 14 and surrounding skin area 14.1.

Figure 2A:
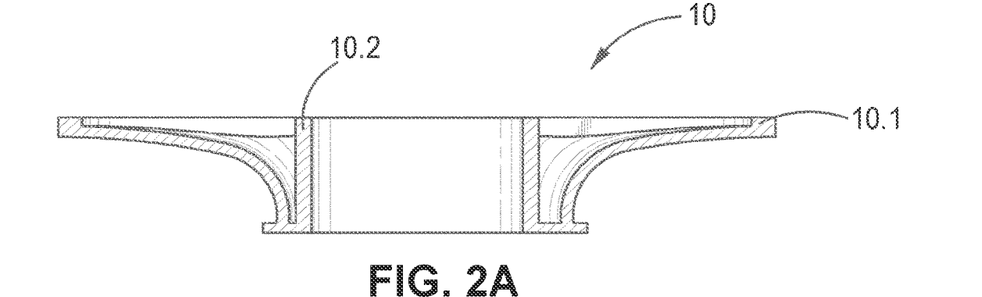
FIG. 2A is a cross-sectional view of a custom ostomy insert mold, made in accordance with one aspect of the disclosure, when viewed across cross-section 2A-2A in FIG. 1A, prior to the addition of molding material.
Figure 2B:
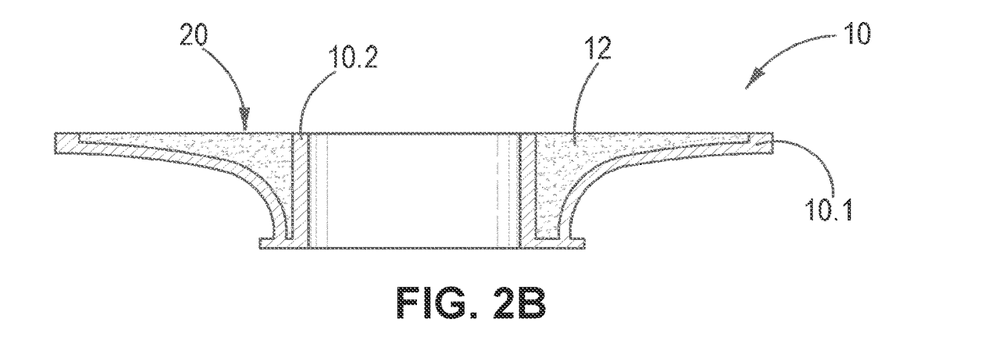
FIG. 2B is a cross-sectional view of a custom ostomy insert mold, made in accordance with one aspect of the disclosure, when viewed across cross-section 2A-2A in FIG. 1A, following the addition of molding material.

The mold 10 includes raised or striated areas 10.3.1 on the surface 10.3 thereof that, when the stoma insert 12 has been molded, produces a complementary hatched, scored, or striated surface on a skin-contacting face 12.2 of the stoma insert 12. The resultant hatched, scored, or striated surface 12.2 assists with channeling sweat, sebum, and other bodily fluids (not shown) away from the stoma 14 and assists in keeping the surrounding skin area 14.1 dry while retaining sufficient purchase when located on the surrounding skin area 14.1 of the patient 16.

It follows that the surface finish 10.3 of the mold 10 can be further optimized, smoothed, roughed, or improved as required. This is achieved in certain embodiments of the disclosure by using chemical vapor processes. In other embodiments, a smooth, non-stick surface may be required and in such a case the surface striations may be smoothed or coated with a non-stick or low-stick compound such as polytetrafluoroethylene, if desired.

In certain embodiments, the mold 10 defines two zones 10.4, 10.5 corresponding in the eventual molded stoma insert 12 to a stoma insert core 12.3, and a circumferentially-extending stoma collar 12.4, respectively, surrounding the stoma insert core 12.3.

Similar to the stoma insert core 12.3, the circumferentially-extending collar 12.4 of the eventual molded stoma insert 12 is shaped and dimensioned to snugly follow the contours of the skin area 14.1 surrounding the stoma 14 in the patient 16, thereby ensuring a snug or light-pressure suction fit between the stoma insert 12 and the stoma 14.

In one embodiment, the stoma insert core 12.3 and collar 12.4 are molded as one, i.e., in unitary fashion. Alternatively, in certain embodiments, and depending on the materials used for molding, the stoma insert core 12.3 and collar 12.4 are molded from two different materials, i.e., in non-unitary fashion. When molded in non-unitary fashion, the stoma insert core 12.3 and the collar 12.4 are each made of moldable materials having differing physico-chemical properties such that the stoma insert core 12.3 is made of a material that is more pliant and resiliently flexible than the material used for the collar 12.4. In this way, the soft core 12.3 of the stoma insert 12 ensures a snug, comfortable fit inside the stoma 14, while the harder peripheral collar 12.4 is resilient enough to securely locate the ostomy pouch 18 proximal the stoma 14.

Scanning the stoma and surrounding skin area is accomplished using computerized tomography, CT. Although CT has been used in this example, the disclosure extends to any suitable surface scanning technology, particularly 3D-scanning techniques, which include ultrasound, optical, X-ray, laser, photoacoustics, blue or white light 3D-scanning, LIDAR, optical coherence tomography, or MRI. The scanning process is performed to create a point cloud of geometric samples of the stoma 14 and surrounding skin surface 14.1 of the patient 16. These points can then be used to extrapolate the shape of the stoma 14 and surrounding skin area 14.1, so that the mold 10 for the stoma insert 12 can be 3D-printed.

Accordingly, the step of manipulating the data is accomplished by converting DICOM data into stereolithography ("STL") files.

In one embodiment of the disclosure, the stoma insert 12 is cast, formed, or molded within the mold using silicone rubber. However, it is within the scope of the disclosure that the stoma insert 12 can be cast, formed, or molded using any one or more of natural rubber, latex, neoprene, polyvinyl chloride, nitrile, synthetic polymer, synthetic resin, synthetic rubber, acrylic-based polymers, or any mixtures thereof.

In one embodiment, the stoma insert is impregnated with an antimicrobial compound, an anti-inflammatory compound, a deodorant compound, and an antiperspirant compound. Each of the compounds is included in the stoma insert 12 in a weight percentage of between 0.001 wt. % and 1 wt. % of the stoma insert 12. When adding a medical or pharmaceutically active compound, it is advantageous, under certain conditions, to impregnate or coat the core of the stoma insert which nests inside the stoma (i.e., bowel opening) or proximal thereto, as many pharmaceutical or medical compounds are not absorbed by skin but rather by the mucosa of bowel. In this example, a slow-release formulation, similar to suppository formulations, may be used to extend the release of the compounds from the stoma insert. Furthermore, compounds that protect the skin may be used, applied to, or impregnated into the stoma insert collar, in other words, differential impregnation or coating of the stoma insert in different parts thereof.

It is contemplated that the antimicrobial compound is selected from any one or more or naturally occurring or synthetic antimicrobial compounds such as antibacterial, bacteriostatic, bacteriolytic, antiviral, and/or antifungal compounds.

A stoma insert with an amount of antimicrobial agent up to about 5 wt. % not only has an effective antimicrobial effect on surfaces of the insert, but also has an antimicrobial effect on surfaces contacted by the insert. Therefore, harmful microbial entities are not only prevented from being transferred from the stoma insert to the skin surface or stoma walls contacted, but microbial entities on that surface may also be reduced, kept static, or eliminated following contact.

In one embodiment, the stoma insert is coated over at least a part thereof with antibodies directed against microbes, particularly antibodies that can bind to, and sequester, microbes that are multiply resistant to current antimicrobials.

The anti-inflammatory compound is, in this embodiment, an antipyretic and analgesic compound, such as a non-steroidal anti-inflammatory drug ("NSAID"). The NSAID is selected from any one or more naturally occurring or synthetic NSAID compounds. Examples of preferred NSAIDs useful in the present disclosure include, but are not limited to: acetylsalicylic acid, ibuprofen, fenbuprofen, fenoprofen, flurbiprofen, indomethacin, ketoprofen, naproxen, their pharmaceutically-acceptable salts, enantiomers thereof, and mixtures thereof. Ibuprofen, indomethacin, acetylsalicylic acid, and naproxen are especially preferred for use in the present disclosure.

Furthermore, in one embodiment, the stoma insert 12 is coated or impregnated with a low-tack, physiologically acceptable adhesive that assists in locating the stoma insert 12 to the stoma 14 or surrounding skin area 14.1.

The deodorant, anti-inflammatory, adhesive, antiperspirant, antimicrobial compounds, as well as the antibodies, are admixed with the moldable material prior to molding. In one embodiment, the compounds are coated on to the mold 10, so that the compounds are transferred to the stoma insert 12 during the molding process.

In one particularly advantageous embodiment of the disclosure, the stoma insert 12 is made from transparent materials such that the skin surrounding the stoma is visible through the insert to allow a care-giver to readily determine whether the skin is inflamed or otherwise subject to an insult or pathological condition which would not readily be discerned without otherwise first having to remove the stoma insert of the disclosure from the stoma.

According to another aspect of the disclosure, there is provided a method of fitting an ostomy bag 18 to a patient 16, the method including the steps of manufacturing a stoma insert 12 in accordance with the disclosure as described herein, fitting the stoma insert 12 to a stoma 14 formed in a patient 16, and attaching an ostomy bag 18 to the stoma insert once it has been fitted to the patient 16. The method of fitting the ostomy bag to the patient includes the step of first providing a bedding material, such as a putty or silicone paste 22, surrounding the stoma insert, prior to fitment of the ostomy bag, to provide further waterproofing of the area, given that there may be a slight elevation between the skin and the ostomy bag/pouch.

As mentioned hereinbefore, and as shown in FIG. 6, the mold 10 has a cross-sectional diameter similar to, or slightly larger than, the opening of an ostomy bag or pouch 18 that is to be fitted to the ostomy insert so that the ostomy pouch or bag 18 can be securely retained in a comfortable, watertight fashion proximal the stoma 14, with minimal discomfort to the patient 16 due to the customized nature thereof.

As used herein, the term "antimicrobial" refers to any naturally-occurring, elemental, synthetic or semi-synthetic compound or composition or mixture thereof, which is safe for human use as used in the methods of this disclosure, and is effective in killing or substantially inhibiting bacteria when used according to the present disclosures. Antibiotics are preferred for use herein. Antibiotics can be generally classified by chemical composition, into the following principal groups: the aminoglycosides, such as gentamicin, neomycin, kanamycin, and streptomycin; the macrolides, such as erythromycin, clindamycin, and rifampin; the penicillins, such as penicillin G, penicillin V, ampicillin and amoxycillin; the polypeptides such as bacitracin and polymyxin; the tetracyclines such as tetracycline, chlortetracycline, oxytetracycline and doxycycline; the cephalosporins such as cephalexin and cephalothin; quinolones such as ciprofloxacin, norfloxacin and ofloxacin; and such miscellaneous antibiotics as chloramphenicol and clindamycin. These antibiotics can generally be said to function in one of four ways: inhibition of cell wall synthesis, alteration of cell wall permeability, inhibition of protein synthesis or inhibition of nucleic acid synthesis.

Other antimicrobials useful herein include the sulfonamides; nitrofurans, such nitrofurazon, nitrofurantoin, and furozolidone; metronidazole, tinidazole, and nimorazole. Antimicrobials among those useful herein are described in Remington's Pharmaceutical Sciences, 18th Edition, pp. 1173-1232 (1990), which is incorporated herein by reference.

While any of these antimicrobials may be used, penicillin, erythromycin, metronidazole, doxycycline, tinidazole, amoxycillin, ampicillin, tetracycline, nitrofurantoin, and mixtures thereof are among the preferred antimicrobials for use in the present disclosure.

Other antimicrobial agents suitable for use in the stoma insert of the present disclosure include, for example, any one or more of diiodomethyl-p-tolylsulfone, 2,4,4'-trichloro-2'-hydroxydiphenyl ethers (triclosan), silver salts, biguanides, chlorohexidene salts, dextran sulfates, quaternary ammonium salts, benzalkoniums, acriflavines, acridine dyes, gentian violet, mercurochromes, extracts of blue green algae, or any mixtures thereof. The antimicrobial agent may be present from about 0.001 wt. % to 5 wt. % of the total weight of the stoma insert. Preferably, the antimicrobial agent is present from about 0.01 wt. % to 1.0 wt. % of the total weight of the insert. More preferably, the antimicrobial agent is present from about 0.02 wt. % to 0.5 wt. % of the total weight of the insert. It is believed that a glove with an amount of antimicrobial agent up to about 5 wt. % not only has an effective antimicrobial effect on surfaces of the insert, but also has an antimicrobial effect on surfaces contacted by the insert. Therefore, harmful microbial entities are not only prevented from being transferred from the insert to the surface contacted, microbial entities on that surface may also be reduced, kept static, or eliminated.

The specific method of administering the antimicrobial, according to the processes of this disclosure, may depend upon such factors as the particular antimicrobial(s) used, the site of infection, the amount of antimicrobial(s) to be administered per day, the presence of any adverse side effects, and the interactions (if any) between the antimicrobial(s) and the bismuth. Thus, the antimicrobial(s) may be administered under the process of this disclosure by single daily doses, or by administration in two, three, four, or more doses per day. Once again, any medicine to be absorbed into the body can be applied to or impregnated into the stoma insert core, while medicine for prophylaxis can be used proximal the surrounding skin, i.e., applied to or impregnated into the stoma insert collar.

The term "NSAID," as used herein, refers to any agent that has anti-inflammatory, antipyretic and/or analgesic properties. Examples of NSAIDs are fully described in U.S. Pat. No. 4,985,459 to Sunshine et al., issued Jan. 15, 1991, incorporated by reference herein in its entirety. For detailed disclosure of the chemical structure, synthesis, side effects, etc., of non-steroidal anti-inflammatory agents, references may be had to standard texts, including "Anti-Inflammatory and Anti-Rheumatic Drugs," K. D. Rainsford, Vol. I-III, CRC Press, Boca Raton (1985), and "Anti-Inflammatory Agents, Chemistry and Pharmacology," 1 R. A. Scherrer, et al., Academic Press, New York (1974), both of which are incorporated by reference herein. Specific NSAIDs useful in the present disclosure include, but are not limited to: the oxicams, such as piroxicam, isoxicam, tenoxicam, sudoxicam, and CP-14,304; the salicylates, such as acetylsalicylic acid, disalcid, benorylate, trilisate, safapryn, solprin, diflunisal, and fendosal; the acetic acid derivatives, such as diclofenac, fenclofenac, indomethacin, sulindac, tolmetin, isoxepac, furofenac, tiopinac, zidometacin, acematacin, fentiazac, zomepiract, clidanac, oxepinac, and felbinac; the fenamates, such as mefenamic, meclofenamic, flufenamic, niflumic, and tolfenamic acids; the propionic acid derivatives, such as ibuprofen, naproxen, benoxaprofen, flurbiprofen, ketoprofen, fenoprofen, fenbufen, indoprofen, pirprofen, carprofen, oxaprozin, pranoprofen, miroprofen, tioxaprofen, suprofen, alminoprofen, and tiaprofenic; and the pyrazoles, such as phenybutazone, oxyphenbutazone, feprazone, azapropazone, and trimethazone. Mixtures of these NSAIDs may also be employed, as well as the pharmaceutically-acceptable salts and esters of these agents.

Another class of NSAIDs is disclosed in U.S. Pat. No. 4,708,966, Loomans, et al., issued Nov. 24, 1987. This patent discloses a class of non-steroidal anti-inflammatory compounds that comprise specifically substituted phenyl compounds, especially substituted 2,6-di-tert-butyl phenol derivatives. For example, compounds selected from 4-(4'-pentyn-3'-one)-2,6-di-t-butylphenol; 4-(5'-hexynoyl)-2,6-di-t-butylphenol; 4-((S)-(−)-3'-methyl-5'-hexynoyl)-2,6-di-t-butyl-phenol; 4-((R)-(+)-3'-methyl-5'-hexynoyl)-2,6-di-t-butylphenol; and 4-(3',3'-dimethoxypropionyl)-2,6-di-t-butylphenol are useful in the present disclosure. Examples of preferred NSAIDs useful in the present disclosure include, but are not limited to: acetylsalicylic acid, ibuprofen, fenbuprofen, fenoprofen, flurbiprofen, indomethacin, ketoprofen, naproxen, their pharmaceutically-acceptable salts, enantiomers thereof, and mixtures thereof. Ibuprofen, indomethacin, acetylsalicylic acid, and naproxen are especially preferred for use in the present disclosure.

It is to be appreciated that reference to "one example" or "an example" of the disclosure is not made in an exclusive sense. Accordingly, one example may exemplify certain aspects of the disclosure, whilst other aspects are exemplified in a different example. These examples are intended to assist the skilled person in performing the disclosure and are not intended to limit the overall scope of the disclosure in any way unless the context clearly indicates otherwise.

It is to be understood that the terminology employed above is for the purpose of description and should not be regarded as limiting. The described embodiment is intended to be illustrative of the disclosure, without limiting the scope thereof. The disclosure is capable of being practiced with various modifications and additions as will readily occur to those skilled in the art.

Various substantially and specifically practical and useful exemplary embodiments of the claimed subject matter are described herein, textually and/or graphically, including the best mode, if any, known to the inventors for carrying out the claimed subject matter. Variations (e.g., modifications and/or enhancements) of one or more embodiments described herein might become apparent to those of ordinary skill in the art upon reading this application.

The inventor(s) expects skilled artisans to employ such variations as appropriate, and the inventor(s) intends for the claimed subject matter to be practiced other than as specifically described herein. Accordingly, as permitted by law, the claimed subject matter includes and covers all equivalents of the claimed subject matter and all improvements to the claimed subject matter. Moreover, every combination of the above described elements, activities, and all possible variations thereof are encompassed by the claimed subject matter unless otherwise clearly indicated herein, clearly and specifically disclaimed, or otherwise clearly contradicted by context.

The use of any and all examples, or exemplary language (e.g., "such as") provided herein, is intended merely to better illuminate one or more embodiments and does not pose a limitation on the scope of any claimed subject matter unless otherwise stated. No language in the specification should be construed as indicating any non-claimed subject matter as essential to the practice of the claimed subject matter.

The use of words that indicate orientation or direction of travel is not to be considered limiting. Thus, words such as "front," "back," "rear," "side," "up," "down," "upper," "lower," "top," "bottom," "forwards," "backwards," "towards," "distal," "proximal," "in," "out" and synonyms, antonyms and derivatives thereof have been selected for convenience only, unless the context indicates otherwise. The inventor(s) envisage that various exemplary embodiments of the claimed subject matter can be supplied in any particular orientation and the claimed subject matter is intended to include such orientations.

The use of the terms "a," "an," "said," "the," and/or similar referents in the context of describing various embodiments (especially in the context of the claimed subject matter) are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted.

Moreover, when any number or range is described herein, unless clearly stated otherwise, that number or range is approximate. Recitation of ranges of values herein are merely intended to serve as a shorthand method of referring individually to each separate value falling within the range, unless otherwise indicated herein, and each separate value and each separate sub-range defined by such separate values is incorporated into the specification as if it were individually recited herein. For example, if a range of 1 to 10 is described, that range includes all values there between, such as for example, 1.1, 2.5, 3.335, 5, 6.179, 8.9999, etc., and includes all sub-ranges there between, such as for example, 1 to 3.65, 2.8 to 8.14, 1.93 to 9, etc.

Accordingly, every portion (e.g., title, field, background, summary, description, abstract, drawing figure, etc.) of this application, other than the claims themselves, is to be regarded as illustrative in nature, and not as restrictive; and the scope of subject matter protected by any patent that issues based on this application is defined only by the claims of that patent.

What is claimed is:

1. A method of manufacturing a custom stoma insert for a patient having a stoma, the method comprising the steps of:
    scanning the stoma and surrounding skin area to generate a three-dimensional scan of the surrounding skin area for which the stoma insert is to be manufactured;
    manipulating scan data obtained from the three-dimensional scan to render a three-dimensional model of the stoma and surrounding skin contours, such that the scan data is suitable for use in an additive manufacturing environment; and
    producing the stoma insert using the scan data with additive manufacturing such that the stoma insert provides a complementary surface closely mirroring the scanned skin contours of the stoma and surrounding skin area, wherein the stoma insert defines a complementary hatched, scored, or striated surface on a skin-contacting face of the stoma insert, the stoma insert including a collar with a central aperture that defines a slightly larger cross-sectional diameter than a cross-sectional diameter of the stoma thereby to ensure a slight friction fit or slight interference fit between the stoma insert and the stoma.

2. The method of claim 1, wherein the step of producing the stoma insert comprises producing a custom mold for the stoma insert using the scan data with additive manufacturing such that the custom mold provides a complementary surface closely mirroring the skin contours of the stoma and surrounding skin area, wherein the custom mold has included therein raised or striated areas that, when the stoma insert has been molded, produces the complementary hatched, scored, or striated surface on a skin-contacting face of the stoma insert, the custom mold including a pillar that corresponds generally to the size of the stoma, wherein the pillar is slightly larger than the stoma to which the stoma insert is to be fitted, such that, when the stoma insert is removed from the custom mold it defines a pillar-like central aperture having a cross-sectional diameter similar to, or slightly larger than, the cross-sectional diameter of the stoma, thereby to ensure a slight friction fit or slight interference fit between the stoma insert and the stoma.

3. The method of claim 2, wherein the step of producing the stoma insert comprises casting a physiologically acceptable moldable material into the custom mold, allowing the physiologically acceptable moldable material to solidify to a desired solidity, and removing the custom stoma insert from the custom mold.

4. The method of claim 3, wherein the stoma insert is cast using one or more of natural rubber, latex, neoprene, polyvinyl chloride, nitrile, synthetic polymer, synthetic resin, synthetic rubber, acrylic-based polymers, or any mixtures thereof.

5. The method of claim 2, wherein the custom mold is shaped and dimensioned to further allow for inclusion of an at least partial circumferentially-extending collar surrounding a core of the stoma insert during a molding process, a collar area of the molded stoma insert in turn being shaped and dimensioned to at least partially cover an area surrounding the stoma sufficiently to ensure sufficient purchase of an ostomy bag on the stoma insert, and wherein the at least partial circumferentially-extending collar is shaped and dimensioned to snugly follow the skin contours of the area surrounding the stoma in the patient, thereby ensuring a snug or light-pressure suction fit between the stoma insert and the stoma core.

6. The method of claim 1, wherein the stoma insert is impregnated or coated with an antimicrobial compound.

7. The method of claim 1, wherein the stoma insert is impregnated or coated with an anti-inflammatory, antipyretic, or analgesic compound, such as a non-steroidal anti-inflammatory drug ("NSAID").

8. The method of claim 1, wherein the stoma insert is impregnated or coated with one or more deodorant compounds.

9. The method of claim 1, wherein the stoma insert is coated or impregnated with a low tack, physiologically acceptable adhesive that may assist in locating the stoma insert to the stoma or surrounding area.

10. The method of claim 1, wherein the stoma insert is coated or impregnated with an antiperspirant compound to control perspiration underneath the stoma insert and to prevent body odor from perspiration or sebaceous excretions of the skin area surrounding the stoma.

11. The method of claim 1, wherein the stoma insert is made from transparent materials such that the skin area surrounding the stoma is visible through the stoma insert to allow a care-giver to readily determine whether the skin area is one or more of inflamed, insult, and subject to a pathological condition which would not readily be discerned without otherwise first having to remove the stoma insert from the stoma.

12. The method of claim 1, wherein producing the stoma insert comprises 3D-printing the stoma insert.

13. The method of claim 2, wherein the step of producing the custom mold is performed using 3D-printing as a preferred form of additive manufacturing.

14. The method of claim 1, wherein the stoma insert and the collar each are made of materials having differing physicochemical properties, wherein the stoma insert is made of a material that is one or more of more pliant and more resiliently flexible than the material used for a stoma insert collar.

15. The method of claim 1, wherein scanning the stoma and surrounding skin area is accomplished using surface scanning technology comprising one or more 3D-scanning techniques selected from a group comprising any one or more of optical, X-ray, laser, photoacoustics, blue or white light 3D-scanning, LIDAR, optical coherence tomography, MRI, tomography, particularly computerized tomography ("CT"), computerized axial tomography ("CAT"), and cone beam computed tomography ("CBCT").

16. The method of claim 15, wherein the one or more 3D-scanning techniques create a point cloud of geometric samples of the stoma and surrounding skin surface of the patient, wherein these points are useable to extrapolate a shape of the stoma and surrounding skin area for use with additive manufacturing.

17. The method of claim 1, wherein manipulating the scan data is accomplished by bringing the scan data into a form suitable for use in 3D-printing using software which converts data in DICOM format to a surface render as an STL file.

18. A stoma insert, formed through the method of claim 1.

19. A method of fitting an ostomy bag to a patient, the method including:
   manufacturing a stoma insert in accordance with the method of claim 1;
   fitting the stoma insert to a patient; and
   attaching an ostomy bag to the stoma insert after the stoma insert has been fitted to the patient.

20. The method of claim 19, wherein fitting the ostomy bag to the patient comprises providing a bedding material surrounding the stoma insert prior to attaching the ostomy bag to the stoma insert.

* * * * *

UNITED STATES PATENT AND TRADEMARK OFFICE
CERTIFICATE OF CORRECTION

PATENT NO. : 11,826,277 B2
APPLICATION NO. : 17/530234
DATED : November 28, 2023
INVENTOR(S) : Jason Jit-Sun Tan It is certified that error appears in the above-identified patent and that said Letters Patent is hereby corrected as shown below:

In the Specification

Column 10, Line 60, change "substituted 2,6-di-tert-butyl" to
-- substituted 2.6-di-tert-butyl --

Signed and Sealed this
Nineteenth Day of March, 2024

Katherine Kelly Vidal
*Director of the United States Patent and Trademark Office*